United States Patent [19]
Duggan et al.

[11] Patent Number: 5,152,686
[45] Date of Patent: Oct. 6, 1992

[54] DENTAL APPLIANCE

[76] Inventors: Calvin Duggan, 1518 Glenmore Dr., Lewisville, Tex. 75067; Ronald E. Jennings, Rte. 1, Box 222B, Argyle, Tex. 76226

[21] Appl. No.: 691,074
[22] Filed: Apr. 25, 1991
[51] Int. Cl.⁵ .............................................. A61C 17/06
[52] U.S. Cl. ........................................ 433/93; 433/29; 433/140
[58] Field of Search ....................... 433/91, 93, 94, 96, 433/136, 140, 29

[56] References Cited

U.S. PATENT DOCUMENTS

| | | | |
|---|---|---|---|
| 2,840,070 | 6/1958 | Tofflemire | 433/29 |
| 2,937,445 | 5/1960 | Erickson | 433/93 |
| 3,171,203 | 3/1965 | Arroyo | 433/140 |
| 3,742,607 | 7/1973 | Johnson | 433/91 |
| 3,924,333 | 12/1975 | Erickson | 433/93 |
| 4,906,188 | 3/1990 | Mosely | 433/93 |

Primary Examiner—Cary E. O'Connor
Attorney, Agent, or Firm—Hubbard, Thurman, Tucker & Harris

[57] ABSTRACT

A dental appliance is provided which includes a bite block made of formable material which includes a tongue stabilizer and a suction tube slidably and removably secured in the bite block for removing debris from the mouth cavity. The appliance may include a raised area for securing the appliance with the patient's teeth during performance of the dental procedures and a posterior vein located in the sidewall of the bite block with an aperture placed in the posterior vein for the suctioning of debris and saliva from the soft palate region of the mouth cavity behind the bite block. A slidably and removably secured rod for transmitting a fiber optic light source for illumination of at least a portion of the mouth cavity may also be included.

7 Claims, 1 Drawing Sheet

DENTAL APPLIANCE

BACKGROUND OF THE INVENTION

This invention relates to a dental appliance which is used for propping open the mouth to permit a dentist to have a wide field of operation, collecting debris or preventing debris from falling into the throat, removing liquid from the mouth of the patient, retraction of the tongue and illumination of the mouth cavity.

In the past, various appliances have been used to isolate or open parts of the mouth to facilitate the performance of dental services. Bite blocks and expansion forceps have been used to hold the patient's jaws open. Rubber dams have typically been used which are flexible pieces of material having holes disposed therein to permit placement down over the teeth into surface contact with the gums, so that the teeth protrude through the holes in the rubber dam.

U.S. Pat. No. 4,053,984 discloses a removable dental appliance which props open the mouth for dental work and includes a tongue deflector and a plurality of orifices which permit the removal of saliva from the mouth when a vacuum source is applied to a saliva ejector which is coupled to the tubular frame.

U.S. Pat. No. 4,281,986 discloses a dental appliance for evacuating debris and liquid from the mouth including a semi-rigid bite block to be gripped by the teeth of the patient as well as a tongue guard.

U.S. Pat. No. 1,122,086 discloses a combined mouth prop, illuminator and suction tube for suctioning saliva from the mouth.

U.S. Pat. No. 1,998,374 is an illuminated dental mouth prop with depressions to engage the teeth and saliva ejector.

U.S. Pat. No. 2,528,458 is a dental mouth prop with a transparent housing for a lamp disposed within the mouth prop.

U.S. Pat. No. 2,800,896 discloses a dental apparatus for illuminating the mouth cavity with an uneven gripping surface and which is partly transparent to allow illumination.

U.S. Pat. No. 3,171,203 discloses a mouth prop device which is provided with a tongue deflector.

U.S. Pat. No. 4,320,745 discloses a laryngoscope with a blade of lucite which transmits light rays for visual inspection of the laryngeal region of the mouth which utilizes fiber optics for illumination.

None of these patents provide for suctioning the soft palate region of the mouth behind the dental appliance. Nor do they disclose illumination of the mouth cavity at selected sites by use of a slidably removable rod means for transmitting fiber optic light energy.

Usually the dental assistant must suction and evacuate the mouth with a hand-held suction device. The mouth illumination devices as previously disclosed are provided at a fixed location in the mouth and thus do not provide for changeable illumination of certain portions of the mouth cavity.

SUMMARY OF THE INVENTION

The invention includes a dental appliance which provides a bite block made of formable material which includes a tongue stabilization means and a suction means slidably and removably secured in the bite block for removing debris from the mouth cavity. The appliance may include a raised area for securing the appliance with the patient's teeth during performance of the dental procedures and a posterior vein located in the sidewall of the bite block with an aperture placed in the posterior vein for the suctioning of debris and saliva from the soft palate region of the mouth cavity behind the bite block. A slidably and removably secured means for transmitting a fiber optic light source for illumination of at least a portion of the mouth cavity may also be included.

DETAILED DESCRIPTION OF THE INVENTION

Figure 1:
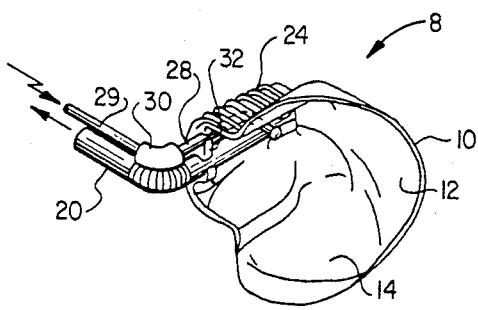
FIG. 1 is a three-quarter perspective view of a dental appliance constructed according to the present invention.
Figure 2:
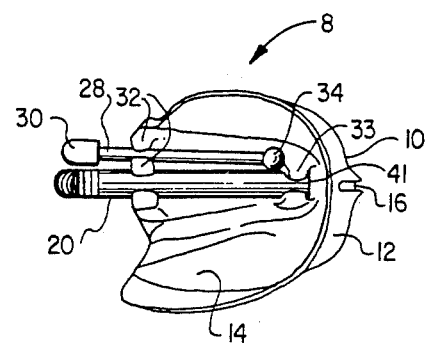
FIG. 2 is a side view of the dental appliance constructed according to the present invention.
Figure 3:
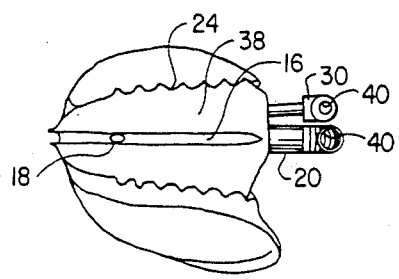
FIG. 3 is a side view of the sidewall of the dental appliance showing the posterior vein.

FIGS. 1-3 illustrate various views of the dental appliance 8 which is the subject of this patent. However, it should be noted that appliance 8 need not be limited to the appliance shown in the drawings herein as these drawings illustrate only the most preferred embodiment of this invention.

FIG. 1 shows dental appliance 8 which comprises bite block 10 having a posterior dam 12 portion of bite block 10 and a tongue stabilization means 14 of bite block 10. A raised area 24 is provided on bite block 10 and may be in the form of ridges or some other suitable gripping or securing surface in order that appliance 8 may be securely retained in the patient's mouth with the patient's teeth.

Figure 5A:
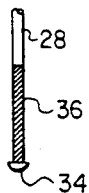
FIG. 5A is a rod for transmitting a fiber optic light source and which is frosted for general illumination.
Figure 5B:
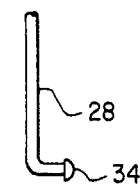
FIG. 5B is a rod for transmitting a fiber optic light source for directed light.
Figure 5C:
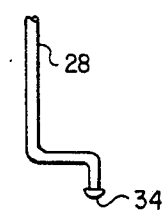
FIG. 5C is a rod for transmitting a fiber optic light source for directed light.

Appliance 8 also includes a first fiber optic light source transmission means 28 which may be slidably and removably secured inside bite block 10. A connector 30 is used to connect first fiber optic light source transmission means 28 with second fiber optic light source transmission means 29. In this way, second means 29 and connector 30 may be removed so that first means 28 can be removed and a different type of first means 28, such as illustrated in FIGS. 5A, 5B and 5C, can be used as a replacement. First fiber optic light source transmission means 28 and second fiber optic light source transmission means 29 are preferably rods which transmit the fiber optic light source into the mouth cavity 22 in FIG. 4. Rod 28 may be inserted in place within bite block 10 by snapping rod 28 into clamp 32 which slidably and removably secures rod 28. Rod 28 can then be slid further in or pulled further out of appliance 8 and mouth cavity 22 in order to position rod 28 so as to illuminate the desired portion of mouth cavity 22. Rod 28 may be removed by snapping rod 28 free from clamp 32. A different rod 28 can then be snapped through clamp 32 into place within the inside of bite block 10. No rod 28 need be used at all, but the use of rod 28 is the preferred embodiment of this invention. FIGS. 5A, 5B and 5C illustrate just a few examples of the different types of rods 28 which may be used with this invention.

FIG. 5A shows rod 28 with frosting 36 which may be accomplished by sandblasting or frosting done in the casting process. A Burring machine can be used to frost the rod. The frosted rod provides for general illumination and the rod contains preferably three-fourths of an inch of sandblasting. The frosting can vary according to the type of light desired and in accordance with finished specifications. Rod 28 may be made of any material which will transmit light, for example, nylon, which is preferred, as well as glass, acrylic, polyvinyl and other suitable materials. One of the advantages of tip 34 is that of accomplishing faster curing among composite porcelains for fillings and tooth forming from what used to take minutes to cure to what is now only seconds.

FIG. 5B provides a rod 28 which is bent in an L-shape or elbow shape so that the light is directed through tip 34 and is directed to a desired portion of mouth cavity 22 in order to provide directed and specific illumination of certain areas within mouth cavity 22. Rod 28 can be slid in and out between clamp 32 in order to move the tip 34 from the back of mouth cavity 22 to the middle or front mouth cavity 22, as desired.

FIG. 5C shows rod 28 bent in an "S" shape so as to provide illumination through tip 34 to be directed to a higher or lower portion of mouth cavity 22 than rod 28 in FIG. 5A and FIG. 5B.

Rod 28 is snapped through clamp 32 so that rod 28 remains removably and slidably secured in mouth cavity 22. Tip 34 prevents rod 28 from slipping past clamp 32. Rod 28 is snapped into place and then connector 30 is attached thereto, and second rod 29 is inserted in orifice 40 of connector 30 in FIG. 3. Connector 30 is a flexible collar, preferably latex, which receives the fiber optic light source through second rod 29.

The fiber optic light source used may be any acceptable source such as halogen or tungsten lighting. The amplitude of light may vary. The light source has an intensity dial of between 75 and 150 watts. Some have a directed light source. A condenser lens may be used in the porthole of the light source to focus the light to the second rod 29.

Referring again to FIG. 1, suction transmission means 20 is removably and slidably inserted through clamp 32 so as to be positioned against the inner surface of sidewall 38. Suction transmission means 20 is elbow or "L" shaped so as to connect with a suction aspirator means in the dental office. The "L" shape of suction transmission means 20 allows the positioning of the suction aspirator means to the side of the patient and doctor so as to be out of the way of the working area. Suction transmission means 20 can be any type of elbow type connector to a suction aspirator, preferably between one-fourth inch and five-sixteenths inch in diameter. The suction transmission means 20 is preferably made of plastic, although latex rubber tubing, paper, cardboard, stainless steel or any other suitable material may be used. A connector 30 may be utilized to connect suction transmission means 20 to the suction aspirator. Suction transmission means 20 may be slid in and out of mouth cavity 22 so as to provide suction to the portion of mouth cavity 22 as desired. Preferably suction transmission means 20 is positioned adjacent to first fiber optic light source transmission means 28 and against the inner wall of sidewall 38. Preferably, suction transmission means 20 is positioned along the line of axis of and parallel to posterior vein 16 which is formed in sidewall 38. Posterior vein 16 is an indentation in sidewall 38 which allows for debris and saliva from the soft palate region of the mouth outside of bite block 10 to travel along posterior vein 16 and to be suctioned through posterior vein aperture 18 through suction transmission means 20 for disposal. Suction transmission means 20 is positioned so as to at least partially cover posterior vein aperture 18 until suction through posterior vein aperture 18 is desired. Then, suction transmission means 20 is slid forward of posterior vein aperture 18 so as to at least partially expose posterior vein 18 and allow suctioning of debris and saliva from outside from the soft palate region of the mouth outside bite block 10.

Referring once again to FIG. 1, posterior dam 12 may be omitted for a laryngoscopy procedure which requires an exposure of the throat region.

Tongue stabilization means 14 acts as a tongue retention device which keeps the tongue in the same spot and also acts as a tongue retractor device which pulls the tongue back so that the tongue will not be in the way of the dental procedures.

Referring to FIG. 2, the inside view of appliance 8 is shown. In this case, appliance 8 is for use in the right half of the patient's mouth and is to be clamped between the patient's teeth on the right side of the patient's mouth. It should be understood that a mirror image of appliance 8 should be used for the left side of the patient's mouth to be clamped between the teeth of the patient's mouth on the left side. Thus, "right-sided" and "left-sided" appliances 8 may be made.

Suction transmission means 20 may be additionally clamped by another clamp 33 toward the back of the inside of bite block 10, but clamp 33 is not required. Suction transmission means can also be additionally secured by the placement of endwall 40 of FIG. 3 into aperture 41 until such time as it is desired to slide suction transmission means 20 in and out at which time suction transmission means 20 is slid out from aperture 41.

Bite block 10 contains posterior dam 12 which is also sometimes called a soft palate shield. This shields the soft palate region from spittle and guards against a gag reflex. Bite block 10 is preferably made of nylon material although bite block 10 may be made of any formable material such as styrofoam (polyurethane), acrylic, thermoplastic, pressed paper or cardboard. Preferably a flexible, malleable material such as nylon is formed by any number of ways, such as vacuum forming, thermal forming, injection molding, pressure forming or molding for wet paper or cardboard and stamp molding for wet paper or cardboard. Preferably, bite block 10 is injection molded from nylon. Raised area 24 is preferably ridges which are formed in the material of bite block 10 although raised area 24 may be accomplished by the placement of indentations in the surface of bite block 10.

Bite block 10 may be made of different sizes and shapes. In the event that bite block 10 is larger than desired, bite block 10 may be heated up by the dentist at chairside and bite block 10 reformed to a different size or fit; for example, for a child. Bite block can then be trimmed to the size desired. This is also helpful for an irregular shaped mouth or palate region, for example, for a high palate.

The dental appliance 8 may be sold as a kit which includes bite block 10 already molded in the desired shape, suction transmission means 20 and possibly connectors 30. The first fiber optic light source transmission means 28 is preferably a rod of nylon which may be sold as a utility kit with any number of different types of rods to choose from, some of which are illustrated in FIGS. 5A, 5B and 5C. It is to be understood that various types of first fiber optic light source transmission means 28 or rods may be designed to desirably illuminate the appropriate portion of the mouth cavity 22.

One advantage of this invention is that all materials are recyclable. Suction transmission means 20 may be used again or thrown away and rods 28 may be interchanged or thrown away.

The purpose of frosting 36 as shown on rod 28 in FIG. 5A is to disperse light for general illumination. Frosting 36 can be varied according to the type of illumination desired. Substantially clear rod 28 of FIG. 5B and 5C provides directed illumination through tip 34 for specific areas within mouth cavity 22, as for example a specific tooth. Rod 28 of FIG. 5C, for example, is particularly useful in providing directed illumination to a one or two tooth area of mouth cavity 22.

Figure 4:
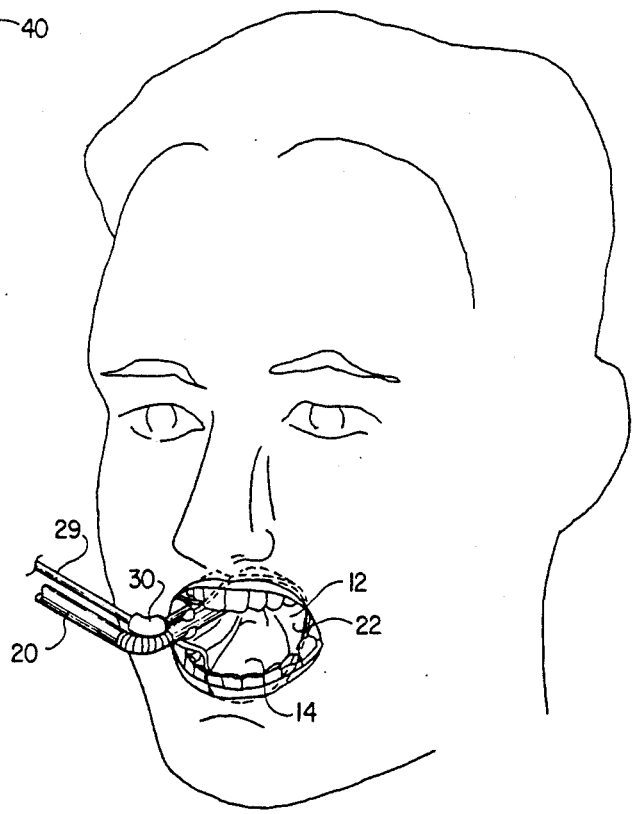
FIG. 4 is a perspective view of the open mouth of a patient showing the dental appliance in place.

FIG. 4 shows appliance 8 in place in a patient's mouth cavity 22. The dotted line shows the outline of bite block 10 which is obstructed from the view in FIG. 4 by the patient's teeth, lips and facial area. The fiber optic light source which is connected to second fiber optic light source transmission means 29, as well as the suction aspirator means which is connected to suction transmission means 20 by a connector 30 of FIG. 3 are both placed to the side of the patient's face so as to stay out of the way of the patient and dentist or dental assistant.

While the invention herein has been described in terms of preferred embodiment, it should be apparent to persons skilled in the art that numerous modifications may be made thereto without departing from the spirit and scope of the invention. Accordingly, it is intended that all such modifications fall within the scope of the claims.

We claim:

1. A dental appliance comprising:
   a bite block made of formable material, wherein said bit block includes a posterior dam, a tongue stabilization means;
   a suction transmission means slidably and removably secured in said bite block for removing debris and saliva from the mouth cavity; and,
   a fiber optic light source transmission means, slidably and removably secured within said bite block, for illumination of at least a portion of said mouth cavity.

2. A dental appliance comprising:
   a bite block made of formable material, wherein said bite block includes a posterior dam, and a tongue stabilization means, a suction transmission means slidably and removably secured in said bite block for removing debris and saliva from the mouth cavity;
   wherein said bite block includes a posterior vein with an aperture placed therein; and,
   wherein said suction transmission means is a tube secured so as to be parallel to said posterior vein.

3. A dental appliance comprising:
   a bite block made of formable material, wherein said bite block includes a posterior dam, and a tongue stabilization means;
   a suction transmission means slidably and removably secured in said bite block for removing debris and saliva from the mouth cavity;
   said bite block including a posterior vein with an aperture placed therein; and,
   wherein said aperture in said posterior vein is positioned in said posterior vein so that said suction transmission means can slide from a position at least partially blocking said aperture from receipt of the suction from said suction transmission means to a position wherein said aperture is in receipt of at least a portion of said suction from said suction transmission means.

4. A dental appliance comprising:
   a bite block made of formable material, wherein said bite block includes a posterior dam, a tongue stabilization means, and a posterior vein with an aperture placed therein;
   a suction transmission means slidably and removably secured in said bite block for removing debris and saliva from the mouth cavity; and
   a slidably and removably secured fiber optic light source transmission means for illumination of at least a portion of said mouth cavity.

5. The dental appliance of claim 4 wherein at least a portion of said bite block includes a raised area for securing said appliance with the patient's teeth.

6. A dental appliance comprising:
   a bite block made of formable material, wherein said bite block includes a posterior dam and a tongue stabilization means;
   a suction transmission means slidably and removably secured in said bite block for removing debris and saliva from the mouth cavity;
   a slidably and removably secured fiber optic light source transmission means for illumination of at least a portion of said mouth cavity; and,
   wherein said fiber optic light source transmission means is a rod made of material which will transmit light to a desired portion of said mouth cavity.

7. A dental appliance comprising:
   a bite block made of formable material, wherein said bite block includes a posterior dam, a tongue stabilization means, a posterior vein with an aperture placed therein, and a raised area for securing said appliance with the patient's teeth;
   a suction transmission means slidably and removably secured in said bite block for removing debris and saliva from the mouth cavity; and
   a slidably and removably secured fiber optic light source transmission means for illumination of at least a portion of said mouth cavity,
   wherein said suction transmission means is a tube secured so as to be parallel to said posterior vein,
   said aperture in said posterior vein is positioned in said posterior vein so that said suction transmission means can slide from a position of at least partially blocking said aperture from receipt of the suction from said suction transmission means to a position wherein said aperture is in receipt of at least a portion of said suction from said suction transmission means; and
   said fiber optic light source transmission means is a rod made of a material which will transmit light to a desired portion of said mouth cavity.

* * * * *